US00RE39723E

(19) United States
(12) Reissued Patent
Bombardelli et al.

(10) Patent Number: US RE39,723 E
(45) Date of Reissued Patent: Jul. 10, 2007

(54) SEMI-SYNTHETIC TAXANES WITH ANTITUMOR AND ANTIANGIOGENETIC ACTIVITIES

(75) Inventors: Ezio Bombardelli, Groppello Cairoli (IT); Alessandro Pontiroli, Milan (IT)

(73) Assignee: Indena S.p.A., Milan (IT)

(21) Appl. No.: 11/158,323

(22) Filed: Jun. 20, 2005

Related U.S. Patent Documents

Reissue of:
(64) Patent No.: 6,589,979
Issued: Jul. 8, 2003
Appl. No.: 10/187,995
Filed: Jul. 3, 2002

U.S. Applications:
(63) Continuation of application No. PCT/EP01/00386, filed on Jan. 15, 2001.

(30) Foreign Application Priority Data

Jan. 18, 2000 (IT) ..... MI2000A0056

(51) Int. Cl.
*A61K 31/337* (2006.01)
*C07D 305/14* (2006.01)

(52) U.S. Cl. ..... 514/449; 549/510; 549/511
(58) Field of Classification Search ..... 514/449; 549/510, 511
See application file for complete search history.

(56) References Cited

U.S. PATENT DOCUMENTS 5,756,776 A * 5/1998 Bombardelli et al. ..... 549/510

FOREIGN PATENT DOCUMENTS

WO WO 96/03394 2/1996

OTHER PUBLICATIONS

Wang et al., The Oxetane Ring in Taxol, J. Org. Chem., 65:1059–1068 (2000).*
Distenfano et al., Antitumor Activity of Paclitaxel (Taxol) Analogs on MDR–positive Human Cancer Cells, Anti–Cancer Drug Design 13(5):489–499 (1998).*
Appendino et al., Synthesis and Evaluation of C–seco Paclitaxel Analogs, Tetrahedron Letters, 38(24):4273–4276 (1997). See p. 4274, compounds 5a–5d.*
Lainer, et al., "New antiangiogenic strategies for the treatment of proliferative synovitis", Expert Opinion Investig. Drugs (2005), 14(1), pp. 1–17.*
International Search Report of PCT/EP01/00386.

* cited by examiner

*Primary Examiner*—Ceila Chang
*Assistant Examiner*—R. James Balls
(74) *Attorney, Agent, or Firm*—Jones Day

(57) ABSTRACT

Seco-baccatin III derivatives of formula:

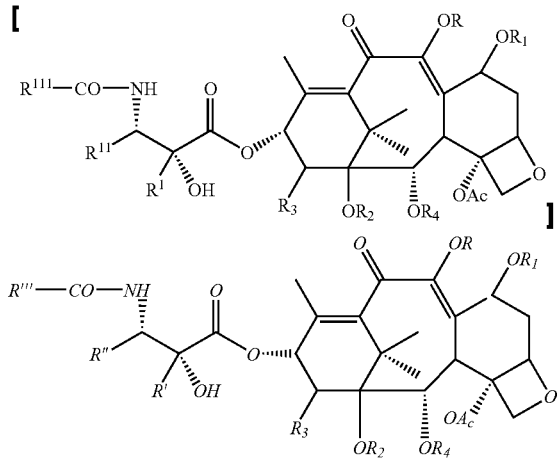

wherein R, $R_1$–$R_4$, [$R^1$] $R'$, [$R^{11}$] $R''$, and [$R^{111}$] $R'''$ are disclosed herein; pharmaceutical compositions comprising seco-baccatin III derivative; and methods for treating cancer, arthritis, and inhibiting angiogenesis in an animal comprising administrating to a patient in need thereof a therapeutically effective amount of a seco-baccatin III derivative are disclosed.

20 Claims, No Drawings

SEMI-SYNTHETIC TAXANES WITH ANTITUMOR AND ANTIANGIOGENETIC ACTIVITIES

Matter enclosed in heavy brackets [ ] appears in the original patent but forms no part of this reissue specification; matter printed in italics indicates the additions made by reissue.

This application is a continuation of PCT/EP01/00386 dated Jan. 15, 2001.

FIELD OF THE INVENTION

The present invention relates to seco-baccatin III derivatives.

TECHNICAL FIELD

Taxane-skeleton diterpenes, in particular Pacliataxel and Docetaxel, are at present used in medicine for the treatment of tumors of different origin.

However, the presently available taxane derivatives have remarkable side effects and also quickly induce resistance, analogously to other antitumor drugs.

The present invention relates to derivatives of seco-baccatine III, which is disclosed in U.S. Pat. No. 5,756,776, characterized by bioavailability through the oral route, reduced toxicity and extremely high antiangiogentic activity.

SUMMARY OF THE INVENTION

The compounds of the present invention have the following general formula (I)

[

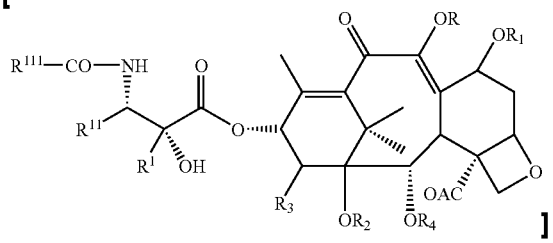

]

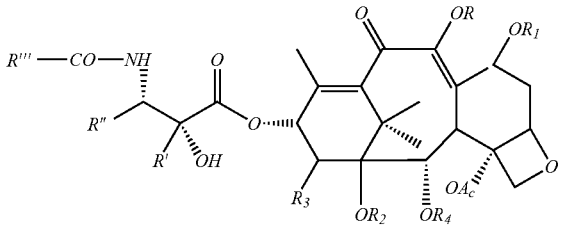

wherein

R and $R_1$, which can be the [sane] *same* or different, are hydrogen, a $C_1$–$C_{18}$ acyl group, an optionally substituted aroyl group or a —$CONR_6R_7$ wherein $R_6$ and $R_7$, which can be the same or different, are $C_1$–$C_4$ alkyl, benzyl, or phenyl groups;

$R_2$ is hydrogen or forms with $R_3$ a carbonate or thiocarbonate residue;

$R_3$ is hydrogen, —$OR_5$ group, wherein $R_5$ is hydrogen, or it forms with $R_2$ a carbonate or thiocarbonate residue;

$R_4$ is a benzoyl group optionally substituted at the meta-position, or hetaroyl group;

[$R^1$] *R′* is hydrogen or a $C_1$–$C_4$ alkyl group;

[$R^{11}$] *R″* is a $C_1$–$C_4$ alkyl, a $C_2$–$C_6$ alkenyl, aryl or hetaryl;

[$R^{111}$] *R‴* is a $C_1$–$C_4$ alkyl, $C_1$–$C_{18}$ acyl, aryl group or tert-butoxy group, with the proviso that R and $R_1$ cannot be both hydrogen.

DETAILED DESCRIPTION OF THE PREFERRED EMBODIMENTS

A $C_1$–$C_{18}$ acyl group is preferably a formyl, acetyl, n-propanoyl, n-hexanoyl group.

An optionally substituted aroyl group is preferably benzoyl, optionally substituted with one or three substituents selected from halogen atoms or $C_1$–$C_4$ alkyl, $C_1$–$C_4$ alkoxy, $C_1$–$C_4$ haloalkyl, $C_1$–$C_4$ haloalkoxy, cyano, nitro groups.

A meta-substituted benzoyl group is preferably a 3-halobenzyl or 3-methoxybenzoyl group.

A hetaroyl group is preferably a 5- or 6-membered heteroaryl having one or two oxygen, nitrogen or sulfur atoms in the ring and substituted with a carbonyl group, for example 2- or 3-thenoyl, nicotinoyl, 2- or 3-furoyl.

Aryl is preferably phenyl and hetaryl is preferably 2- or 3-furyl, 2- or 3-thienyl, 2- 3- or 4-pyridyl.

A preferred group of compounds of formula (I) is that in which:

R and $R_1$, which are the same, are a $C_1$–$C_{18}$ acyl group, an optionally substituted benzoyl group as defined above or a $CONR_6R_7$ group, more preferably R and $R_1$ are acetyl or 3,4,5-trimethoxy-benzoyl;

$R_2$ is hydrogen;

$R_3$ is hydrogen;

$R_4$ is benzoyl;

R' is hydrogen or methyl;

R" is $C_1$–$C_4$ alkyl or $C_2$–$C_6$ alkenyl, more preferably isobutyl or isobutenyl;

R'" is a tert-butoxy group.

A further group of preferred compounds is the one in which R is hydrogen and $R_1$ is an acyl, aroyl or $CONR_6R_7$ group as defined above, $R_2$ and $R_3$ are hydrogen, $R_4$ is benzoyl, $R_1$ is hydrogen or methyl, R" is $C_1$–$C_4$ alkyl or $C_2$–$C_6$ alkenyl and R'" is tert-butoxy.

The esterification of the hydroxyls at C-7 and C-9 induces, compared with known compounds, an increase in the cytotoxic activity on the resistant cell lines as well as improved absorption through the oral route. The compounds of the invention are less potent than Paclitaxel, taken as the reference drug, in binding with tubulin, while keeping comparable cytotoxicity on the sensitive cancer lines. These compounds mainly differ from those of prior art in the antiangiogenetic activity. Table shows the in vivo activity of some C-seco-10-dehydro-10-deacetyl-7,9-bisacetyl-baccatine III and C-seco-10-dehydro-10-deacetyl-7,9-bisacetyl-1,14-carbonate-baccatine III derivatives having the same isoserine chain.

The antiangiogenic activity was evaluated by means of the Matrigel test, in which angiogenesis is induced by FGF-2 (150 mg/pellet) adsorbed on a Matrigel pellet (12.5 mg/ml, 0.5 mL) injected subcutaneously in C57BL6N mice.

The tested compound was administered through the oral route daily or through the intraperitoneal route on alternate days, at the shown concentration. After 7 days, the angiogenic response was evaluated by measuring the hemoglobin content in the pellets, according to the procedure by Drabkin.

TABLE

In vivo antiangiogenetic activity of the compound of example II.

| Compound | Hemoglobin g/dl | % |
|---|---|---|
| Control | 0.01 ± 0.001 | — |
| FGF-2 | 0.03 ± 0.001 | +300 |
| Example II | | |
| 90 mg/kg i.p. | 0.015 ± 0.001 | −50 |
| 150 mg/kg p.o. | 0.009 ± 0.001 | −70 |
| Example VII | | |
| 50 mg/kg i.p. | 0.014 | −40 |
| 100 mg/kg p.o. | 0.009 | −70 |

The compounds of the invention are prepared by reacting C-seco-10-dehydro-10-deacetyl-7,9-hydroxy baccatine III described in U.S. Pat. No. 5,756,776 with a carboxylic acid reactive derivative (chloride or anhydride), according to known acylation methods.

The C7 and C9 diesters can be prepared by using at least two equivalents of the reactive derivative. The carbamate groups can be introduced with conventional methods, for example by reaction with phosgene and an amine of formula $R_6R_7NH$.

The resulting compounds are then reacted, according to known procedures, with an isoserine derivative, usually an oxazolidine derivative, which, by acid treatment under mild conditions gives compounds (I).

The compounds of the invention are characterized by low systemic toxicity: at doses effective in inhibiting the tumor growth they induce neither weight loss nor evident neurotoxicity; in the nude mouse transplanted with human tumor cells, a dose of Paclitaxel, used as the reference drug, exerting the same antitumor activity, also induces tremors and weight loss up to 20%.

The compounds of the present invention, thanks to their high water solubility, can be easily formulated in injectable preparations.

Compounds (I) can also be formulated in the form of conventional oral compositions (capsules or tablets).

Thanks to their low toxicity, compounds (I) can be administered intravenously at dosages up to 600 mg/m$^2$ and orally at dosages up to 1000 mg/m$^2$. Dosages can be decreased to 50 mg/m$^2$ in the treatment of rheumatoid arthritis.

The following examples further illustrate the invention without limiting its scope.

EXAMPLE I

Preparation of C-seco-10-dehydro-10-deacetyl-7,9-bis-acetyl-baccatine III

A solution of 300 mg of 10-dehydro-10-deacetylbaccatine III in 5 ml of methanol is added with 1 equiv. of $CeCl_3.3H_2O$ and the reaction mixture is stirred for 10 min. After complete dissolution, 80 mg of $NaBH_4$ are added in small portions. After 10 min the solution is treated with an equal volume of a $NH_4Cl$ aqueous solution and extracted with $CH_2Cl_2$. The chlorinated solvent is removed, the residue is taken up in 1 ml of pyridine, cooled to 0° C. in 1 h, then added with 150 mg of acetic anhydride. The solution is left to stand for 2 h at 0° C., then diluted with 10 ml of water and back-extracted with $CH_2Cl_2$. The chlorinated solvent is distilled off under vacuum and the residue is chromatographed on silica gel eluting with a mixture of n-hexane/ethyl acetate to obtain 260 mg of C-seco-10-dehydro-10-deacetyl-7,9-bis-acetyl-baccatine III (m/z 630).

EXAMPLE II

Preparation of 13-[(2R, 3S)-3-iso-butyl-2-hydroxy-3-tert-butoxycarbonylamino-propanoyl]-C-seco-10-dehydro-10-deacetyl-7,9-bis-acetyl-baccatine III 630 mg of C-sero-10-dehydro-10-deacetyl-7,9-bis-acetyl-baccatine III are dissolved in 5 ml of toluene and added with 335 mg of dicyclohexylcarbodiimide (DCC), 500 mg of (4S,5R)-N-Boc-2-(2,4-dimethoxyphenyl)-4isobutyl-5-oxazolidine-carboxylic acid and 20 mg of 4-dimethylaminopyridine. The solution is heated at 60° C. for 24 h, then treated with ethyl acetate and a $NaHCO_3$ saturated solution. The organic phase is dried and filtered through silica gel to remove urea. The solvent is evaporated to dryness under vacuum and the residue is taken up in methanol/hydrochloric acid, keeping a temperature of 0° C. for 1 h. The solution is neutralized to pH 5, then diluted with water and the desired compound is back-extracted with $CH_2Cl_2$. The solvent is evaporated off to obtain 700 mg of 13-[(2R, 3S)-3-iso-butyl-2-hydroxy-3-tert-butoxycarbonylamino-propanoyl]-C-seco 10-dehydro-10-deacetyl-7,9-bis-acetyl-baccatine III.

EXAMPLE III

Preparation of 13-[(2R, 3S)-3-phenyl-2-hydroxy-3-tert-butoxycarbonylamino-propanoyl]-C-seco-10-dehydro-10-deacetyl-7,9-bis-acetyl-baccatine III 630 mg of C-seco-10-dehydro-10-deacetyl-7,9-bis-acetyl-baccatine III are dissolved in 5 ml of toluene and added with 335 mg of DCC, 525 mg of (4S,5R)-N-Boc-2-(2,4-dimethoxyphenyl)4-isobutyl-5-oxazolidine-carboxylic acid and 20 mg of 4dimethylaminopyridine. The solution is heated at 60° C. for 24 h, then treated with ethyl acetate and a $NaHCO_3$ saturated solution. The organic phase is dried and filtered through silica gel to remove urea. The solvent is evaporated to dryness under vacuum and the residue is taken up in methanol/hydrochloric acid, keeping a temperature of 0° C. for 1 h. The solution is neutralized to pH 5, then diluted with water and the desired compound is back-extracted with $CH_2Cl_2$. The solvent is evaporated off to obtain 700 mg of 13-[(2R, 3S)-3-iso-butyl-2-hydroxy-3-tert-butoxycarbonylamino-propanoyl]-C-seco-10-dehydro-10-deacetyl-7,9-bis-acetyl-baccatine III, which is crystallized from ethyl acetate to yield 645 mg of pure compound.

EXAMPLE IV

Preparation of C-seco-10-dehydro-10-deacetyl-7,9-bis-trimethoxybenzoyl-baccatine III A solution of 546 mg of C-seco-10-dehydro-10-deacetyl-baccatine III in 3 ml of pyridine is added with 575 mg of trimethoxybenzoyl chloride in small portions. After 3 h the solution is poured into 30 ml of water and extracted with $CH_2Cl_2$; the organic phase is washed with acids until pyridine is completely removed. The solvent is evaporated off to obtain 905 mg of C-seco-10-dehydro-10-deacetyl-7,9-bis-trimethoxybenzoyl-baccatine III. (m/z 936).

EXAMPLE V

Preparation of 13-[(2R, 3S)-3-phenyl-2-hydroxy-3-tert-butoxycarbonylamino-propanoyl]-C-seco-10-dehydro-10deacetyl-7,9-bis-trimethoxybenzoyl-baccatine III 930 mg of 13-[(2R, 3S)]-C-seco-10-dehydro-10-deacetyl-7,9-bis-trimethoxy-benzoyl-baccatine III are dissolved in 15 ml of toluene and added with 335 mg of DCC, 525 mg of (4S, 5R)-N-boc-2-(2,4-dimethoxyphenyl)4isobutyl-5-oxazolidinecarboxylic acid and 20 mg of 4-dimethylaminopyridine. The solution is heated at 60° C. for 24 h, then treated with ethyl acetate and a $NaHCO_3$ saturated solution. The organic phase is dried and filtered through silica gel to remove urea. The solvent is evaporated to dryness under vacuum and the residue is taken up in methanol/hydrochloric acid, keeping a temperature of 0° C. for 1 h. The solution is neutralized to pH 5, then diluted with water and the desired compound is back-extracted with $CH_2Cl_2$. The solvent is evaporated off to obtain 940 mg of 13-(2R, 3S)-3-isobutyl-2-hydroxy-3-tert-butoxycarbonylamino-propanoyl]-C-seco-10-dehydro-10-deacetyl-7,9-bis-trimethoxybenzoyl-baccatine III, which is crystallized from ethyl acetate to yield 878 mg of pure compound.

EXAMPLE VI

Preparation of C-seco-10-dehydro-10-deacetyl-7,9-bis-acetyl-baccatine III 1,14-carbonate 1 g of 10-deacetyl-14β-hydroxybaccatine III *1,14 carbonate*, prepared as disclosed in U.S. Pat. No. 5,698,712, are dissolved in methanol and treated with 6 g of Cu(OAc)2 and the reaction mixture is stirred for 120 hrs. The salt is filtered off, the solvent is removed and the residue is chromatographed on silica gel column, eluting with a 6:4 mixture of hexane/ethyl acetate, to obtain 0.9 g of 10-dehydro-10-deactyl-14,β-hydroxy-baccatine III 1,14carbonate (M+568). 300 mg of this compound are dissolved in methanol and treated with 1 equiv. of $CeCl_3.3H_2O$ and the reaction mixture is stirred for 10 min. After complete dissolution, 80 mg of $NaBH_4$ are added in small portions. After 10 min the solution is treated with an equal volume of a $NH_4Cl$ aqueous solution and extracted with $CH_2Cl_2$. The chlorinated solvent is removed, the residue is taken up in 1 ml of pyridine, cooled to 0° C. in 1 h, then added with 150 mg of acetic anhydride under stirring. The solution is left to stand for 2 h at 0° C., then diluted with 10 ml of water and back-extracted with $CH_2Cl_2$. The chlorinated solvent is distilled off under vacuum and the residue is chromatographed on silica gel eluting with a mixture of n-hexane/ethyl acetate to obtain 250 mg of C-seco-10-dehydro-10-deacetyl-7,9-bis-acetyl-baccatine III 1,14-carbonate (m/z 658).

EXAMPLE VII

Preparation of 13-[(2R, 3S)-3-isobutyl-2-hydroxy-3-tert-butoxycarbonylamino-propanoyl]-C-seco-10-dehydro-10-deacetyl-7,9-bis-acetyl-baccatine III 1,14-carbonate 600 mg of C-seco-10-dehydro-10-deacetyl-7,9-bis-acetyl-baccatine III 1,14-carbonate are treated as described in Example II, to obtain 680 mg of the title compound.

What is claimed is:

[1. A compound of formula:

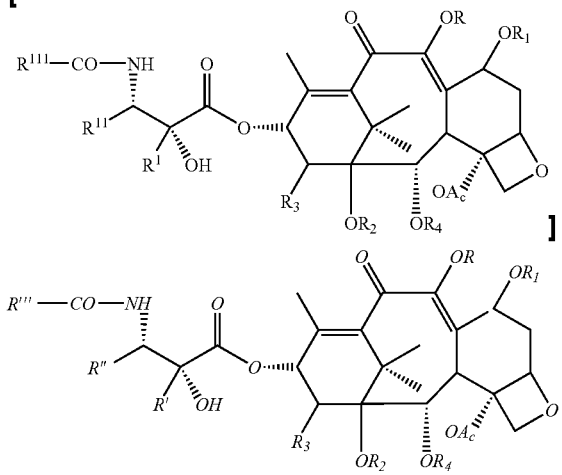

]

wherein R and $R_1$ are each independently hydrogen, a $C_1$–$C_{18}$ acyl group, an aroyl group which may be substituted or unsubstituted, or —$CONR_6R_7$;

$R_2$ is hydrogen or $R_2$ forms a carbonate [or thiocarbonate] with $R_3$;

$R_3$ is [hydrogen,] *hydrogen or* —OH, or $R_3$ forms a carbonate [or thiocarbonate] with $R_2$;

$R_4$ is a benzoyl group which is unsubstituted or substituted at the meta position or a hetaroyl group;

$R_6$ and $R_7$ are a $C_1$–$C_4$ alkyl group, a benzyl group, or a phenyl group;

[$R^1$] $R'$ is hydrogen or a $C_1$–$C_4$ alkyl group;

[$R^{11}$] $R''$ is a $C_1$–$C_4$ alkyl group, a $C_2$–$C_6$ alkenyl group, an aryl group, or a hetaryl group; and

[$R^{111}$] $R'''$ is a $C_1$–$C_4$ alkyl group, a $C_1$–$C_{18}$ acyl group, an aryl group, or a tert-butoxy group, with the proviso that both R and $R_1$ cannot be hydrogen.

2. The compound of claim 1, wherein both R and $R_1$ are a $C_1$–$C_{18}$ acyl group, an aroyl group which may be substituted or unsubstituted, or —$CONR_6R_7$;

$R_2$ is hydrogen;

$R_3$ is hydrogen;

$R_4$ is benzoyl;

[$R^1$] $R'$ is hydrogen or methyl;

[$R^{11}$] $R''$ is a $C_1$–$C_4$ alkyl group or a $C_2$–$C_6$ alkenyl group; and

[$R^{111}$] $R'''$ is a tert-butoxy group.

3. The compound of claim 2, wherein R and $R_1$ are acetyl or 3,4,5-trimethoxybenzoyl.

4. The compound of claim 2, wherein [$R^{11}$] $R''$ is isobutyl or isobutenyl.

5. The compound of claim 1, wherein R and $R_1$ are acetyl or 3,4,5-trimethoxybenzoyl and [$R^{11}$] $R''$ is isobutyl or isobutenyl.

6. The compound of claim 1, wherein R is hydrogen;

$R_1$ is a $C_1$–$C_{18}$ acyl group, an aroyl group which may be substituted or unsubstituted, or —$CONR_6R_7$;

$R_2$ and $R_3$ are hydrogen;

$R_4$ is benzoyl;

[$R^1$] $R'$ is hydrogen or methyl;

[$R^{11}$] $R''$ is a $C_1$–$C_4$ alkyl group, a $C_2$–$C_6$ alkenyl group; and

[$R^{111}$] $R'''$ is a tert-butoxy group.

7. The compound of claim 1, selected from the group consisting of

[13-[(2R, 3S)-3-iso-butyl-2-hydroxy-3-tert-butoxycarbonylamino-propanoyl]-C-seco-10-dehyrdo-10-deacetyl-7,9-bis-acetyl-baccatine III]

*13-[(2R, 3S)-3-iso-butyl-2-hydroxy-3-tert-butoxycarbonylamino-propanoyl]-C-seco-10-dehydro-10-deacetyl-7,9-bis-acetyl-baccatine III*;

[13-[(2R, 3S)-3-phenyl-2-hydroxy-3-tert-butoxycarbonylamino-propanoyl]-C-seco-10-dehyrdo-10-deacetyl-7,9-bis-acetyl-baccatine III]

*13-[(2R, 3S)-3-phenyl-2-hydroxy-3-tert-butoxycarbonylamino-propanoyl]-C-seco-10-dehydro-10-deacetyl-7,9-bis-acetyl-baccatine III*;

[13-[(2R, 3S)-3-phenyl-2-hydroxy-3-tert-butoxycarbonylamino-propanoyl]-C-seco-10-dehyrdo-10-deacetyl-7,9-bis-trimethoxybenzoyl-baccatine III]

*13-[(2R, 3S)-3-phenyl-2-hydroxy-3-tert-butoxycarbonylamino-propanoyl]-C-seco-10-dehydro-10-deacetyl-7,9-bis-trimethoxybenzoyl-baccatine III*;

[13-[(2R, 3S)-3-phenyl-2-hydroxy-3-tert-butoxycarbonylamino-propanoyl]-C-seco-10-dehyrdo-10-deacetyl-7,9-bis-acetyl-baccatine III 1,14-carbonate]

*13-[(2R, 3S)-3-phenyl-2-hydroxy-3-tert-butoxycarbonylamino-propanoyl]-C-seco-10-dehydro-10-deacetyl-7,9-bis-acetyl-baccatine III 1,14-carbonate*.

8. A pharmaceutical composition comprising the compound of claim 1 and a pharmaceutically acceptable carrier.

9. A pharmaceutical composition comprising the compound of claim 2 and a pharmaceutically acceptable carrier.

10. A pharmaceutical composition comprising the compound of claim 3 and a pharmaceutically acceptable carrier.

11. A pharmaceutical composition comprising the compound of claim 4 and a pharmaceutically acceptable carrier.

12. A pharmaceutical composition comprising the compound of claim 5 and a pharmaceutically acceptable carrier.

13. A pharmaceutical composition comprising the compound of claim 6 and a pharmaceutically acceptable carrier.

14. A pharmaceutical composition comprising the compound of claim 7 and a pharmaceutically acceptable carrier.

15. A method of treating cancer comprising administering to a patient in need thereof a therapeutically effective amount of the compound of claim 1.

16. The method of claim 15, wherein the compound is administered to the patient intravenously in an amount of up to 600 $mg/m^2$.

17. The method of claim 15, wherein the compound is administered to the patient orally in an amount of up to 1000 $mg/m^2$.

18. A method of treating *rheumatoid* arthritis comprising administering to a patient in need thereof a therapeutically effective amount of the compound of claim 1.

19. The method of claim 18, wherein the compound is administered to the patient in an amount of up to 50 $mg/m^2$.

20. A method of inhibiting angiogenesis comprising administering to a patient in need there of a therapeutically effective amount of the compound of claim 1.

* * * * *